United States Patent
Thorel (10) Patent No.: US 11,617,708 B2
(45) Date of Patent: Apr. 4, 2023

(54) COSMETIC COMPOSITION CAPABLE OF STRENGTHENING EPIDERMAL TIGHT JUNCTIONS FOR THE PREVENTION AND/OR TREATMENT OF ATOPIC DERMATITIS

(71) Applicants: NAOS INSTITUTE OF LIFE SCIENCE, Aix-en-Provence (FR); Jean-Noël Thorel, Paris (FR)

(72) Inventor: Jean-Noël Thorel, Paris (FR)

(73) Assignees: Jean-Noël Thorel, Paris (FR); NAOS INSTITUTE OF LIFE SCIENCE, Aix-en-Provence (FR)

( * ) Notice: Subject to any disclaimer, the term of this patent is extended or adjusted under 35 U.S.C. 154(b) by 0 days.

(21) Appl. No.: 17/557,477

(22) Filed: Dec. 21, 2021

(65) Prior Publication Data
US 2022/0202675 A1 Jun. 30, 2022

(30) Foreign Application Priority Data
Dec. 24, 2020 (FR) ...................................... 2014142

(51) Int. Cl.
| A61K 8/44 | (2006.01) |
| A61K 8/68 | (2006.01) |
| A61Q 17/04 | (2006.01) |
| A61Q 19/00 | (2006.01) |

(52) U.S. Cl.
CPC ............... *A61K 8/44* (2013.01); *A61K 8/68* (2013.01); *A61Q 17/04* (2013.01); *A61Q 19/00* (2013.01)

(58) Field of Classification Search
None
See application file for complete search history.

(56) References Cited

U.S. PATENT DOCUMENTS

2008/0213323 A1* 9/2008 De Lacharriere ....... A61P 17/02
514/474
2012/0172326 A1 7/2012 Da Luz Moreira et al.

FOREIGN PATENT DOCUMENTS

| EP | 2691090 A2 | 2/2014 |
| EP | 2704704 A1 | 3/2014 |
| FR | 2831059 A1 | 4/2003 |
| JP | 2000264825 A | 9/2000 |
| JP | 2000264829 A | 9/2000 |
| JP | 2001026530 A | 1/2001 |
| WO | 2012131341 A2 | 10/2012 |
| WO | 2012150269 A1 | 11/2012 |
| WO | 2014/023895 A2 | 2/2014 |

OTHER PUBLICATIONS

Mao-Qiang, Man, et al. "Optimization of physiological lipid mixtures for barrier repair." Journal of Investigative Dermatology 106.5 (1996): 1096-1101.
Batista, D.I.S., Perez, L., Orfali, R.L., Zaniboni, M.C., Samorano, L.P., Pereira, N.V., Sotto, M.N., Ishizaki, A.S., Oliveira, L.M.S., Sato, M.N., et al. (2015). Profile of skin barrier proteins (filaggrin, claudins 1 and 4) and Th1/Th2/Th17 cytokines in adults with atopic dermatitis. J. Eur. Acad. Dermatol. Venereol. 29: 1091-1095.
Brandner, J.M., Kief, S., Grund, C., Rendl, M., Houdek, P., Kuhn, C., Tschachler, E., Franke, W.W., and Moll, I. (2002). Organization and formation of the tight junction system in human epidermis and cultured keratinocytes. Eur. J. Cell Biol. 81: 253-263.
Cipriani, F., Dondi, A., and Ricci, G. (2014). Recent advances in epidemiology and prevention of atopic eczema. Off. Publ. Eur. Soc. Pediatr. Allergy Immunol. 25: 630-638.
Gruber, R., Börnchen, C., Rose, K., Daubmann, A., Volksdorf, T., Wladykowski, E., Vidal-Y-Sy, S., Peters, E.M., Danso, M., Bouwstra, J.A., et al. (2015). Diverse regulation of claudin-1 and claudin-4 in atopic dermatitis. Am. J. Pathol. 185:2777-2789.
Halling-Overgaard, A.-S., Kezic, S., Jakasa, I., Engebretsen, K.A., Maibach, H., and Thyssen, J.P. (2017). Skin absorption through atopic dermatitis skin: a systematic review. Br. J. Dermatol. 177: 84-106.
Mack, M.R., and Kim, B.S. (2018). The Itch-Scratch Cycle: A Neuroimmune Perspective. Trends Immunol. 39: 980-991.
Mochizuki, H., Lavery, M.J., Nattkemper, L.A., Albomoz, C., Valdes Rodriguez, R., Stull, C., Weaver, L., Hamsher, J., Sanders, K.M., Chan, Y.H., et al. (2019). Impact of acute stress on itch sensation and scratching behaviour in patients with atopic dermatitis and healthy controls. Br. J. Dermatol. 180: 821-827.
Weidinger, S., Beck, L.A., Bieber, T., Kabashima, K., and Irvine, A.D. (2018). Atopic dermatitis. Nat. Rev. Dis. Primer 4: 1.
Niessen, Carien M. "Tight junctions/adherens junctions: basic structure and function." Journal of investigative dermatology 127.11 (2007): 2525-2532.
Kuo, I-Hsin, et al. "Activation of epidermal toll-like receptor 2 enhances tight junction function: implications for atopic dermatitis and skin barrier repair." Journal of Investigative Dermatology 133.4 (2013): 988-998.

* cited by examiner

*Primary Examiner* — Nannette Holloman
(74) *Attorney, Agent, or Firm* — Meunier Carlin & Curfman LLC (57) ABSTRACT

The invention concerns a composition, advantageously cosmetic, comprising:
  at least one basic amino acid selected from the group constituted by arginine, lysine, histidine, ornithine, hydroxyproline and one of their salts; and
  at least one glycosylceramide,
and its use for preventing and/or treating atopic dermatitis.

20 Claims, 1 Drawing Sheet

COSMETIC COMPOSITION CAPABLE OF STRENGTHENING EPIDERMAL TIGHT JUNCTIONS FOR THE PREVENTION AND/OR TREATMENT OF ATOPIC DERMATITIS

TECHNICAL FIELD OF THE INVENTION

The invention relates to the field of skin care, and more particularly to the treatment of inflammatory skin disorders. More precisely, the invention concerns a composition, which is advantageously cosmetic, for the prevention and/or treatment of atopic dermatitis.

PRIOR ART

Atopic dermatitis, or atopic eczema, is a prurigenic chronic inflammatory dermatitis, i.e. an inflammatory skin disorder which is characterized by intense and chronic itching and by recurrent, episodic eczematous lesions (Mack and Kim, 2018; Weidinger et al., 2018). This disease is linked to anomalies in the function of the skin barrier or in fact to the possible appearance of other symptoms such as allergic rhinitis, asthma, or hypersensitivity to environmental allergens which are normally tolerated in healthy subjects.

A change in the barrier function of the epidermis plays a key role in the initiation of atopic dermatitis (Kuo et al., 2013). In fact, this lack of a barrier function for the epidermis induces a vicious circle of itching and scratching (Mochizuki et al., 2019), which increases the permeability of allergens, bacteria and viruses (Cipriani et al., 2014; Halling-Overgaard et al., 2017), which in turn act as mediators in the increased inflammation process.

Tight junctions (or zonula occludens) are intercellular junctions which are crucial to epithelial adhesion (or intercellular adhesion) and the barrier function. They are dynamic transmembrane complexes which open and close. These tight junctions are composed of structural proteins, proteins associated with the cytoskeleton and proteins participating in signaling and cellular polarity mechanisms (Niessen, 2007).

In particular, the tight junctions are constituted by transmembrane proteins such as claudins, occludins junction adhesion molecules (JAMs), and tricellulins, which are structural proteins which are similar to occludins; and cytosolic proteins such as the zonula occludens (ZO) proteins, cingulins, the multiple-PDZ domain protein 1 (MUPP1) protein, or in fact the Membrane-Associated Guanylate kinase with Inverted orientation (MAGI) protein.

Tight junctions are found in particular in the granular layer (or stratum granulosum) of the epidermis (Brandner et al., 2002).

The principal function of tight junctions in the skin is to establish a second skin barrier which intervenes instantaneously upon rupture of the horny layer (or stratum corneum) of the skin.

Several scientific studies have shown that the expression of several of the proteins of which the tight junctions are composed is modified in the skin of patients afflicted with atopic dermatitis; in particular, the expression of claudin-1 is significantly reduced in the lesional zones of patients with atopic dermatitis (Batista et al., 2015; Gruber et al., 2015; Yuki et al., 2011).

The foregoing shows that restoring the expression and functionality of tight junctions offers a novel way of strengthening or re-establishing the barrier function of the skin, and for this reason, of preventing and/or treating atopic dermatitis.

By way of example, documents EP 2 691 090 and EP 2 704 704 respectively describe the use of cosmetic active principles (plant polyphenols, flavonoids or cis-urocanic acid) and probiotic bacteria to strengthen the tight junctions with the aim of treating atopic dermatitis.

However, the solutions proposed by those documents correspond to undefined compositions of plant extracts and bacterial lysates which could give rise to allergic or inflammatory reactions following application to the human skin and in which the composition can vary significantly from batch to batch.

Thus, there is a clear need for the development of a composition comprising pure dermatologically active compounds which contribute to re-establishing the functionality of the fight junctions in the pre-atopic and atopic skin, which also have high titres of active molecules enabling atopic dermatitis to be prevented and/or treated, in particular in the long term, and which are safe for topical human use, i.e. entirely compatible with the skin, and ideally biomimetic, i.e. identical to the constituents of human skin.

DESCRIPTION OF THE INVENTION

The Applicant has shown that, surprisingly, several dermatological active principles which are entirely safe and suitable for human cosmetic use can overcome the disadvantages and meet the needs described above.

In general, the objective of the invention is to respond to a genuine need, in particular a cosmetic need, while hydrating and soothing the skin, reducing sensations of discomfort and, in the end, improving the appearance of the skin.

In particular, the invention aims to treat atopic dermatitis in order to improve the appearance of the skin and reduce imperfections.

More precisely, the Applicant has shown that the compounds or active principles comprised in the composition in accordance with the invention act in a synergistic manner to induce the expression of claudin-1, a key structural protein in tight junctions. These compounds, which are completely biomimetic, are capable of being used in the formulation of derma-cosmetic products adapted to the prevention and/or treatment of atopic dermatitis.

In the context of the invention, the term "active principle" designates a substance or a compound which has biological and/or therapeutic properties which subtend a physiological effect.

The active principle is distinct from the at least one excipient which is present in the composition in accordance with the invention.

The term "excipient" designates a substance other than the active principle which provides the composition with properties, in particular consistency, galenical properties and/or vectorisation properties of the active principle.

In the context of the invention, the term "biomimetic compound" designates a compound which exists naturally on/in a healthy skin and its appendages or which, after hydrolysis or oxidation/reduction, is transformed into compounds which also exist naturally on/in a healthy skin and its appendages. In accordance with the invention, this compound is considered in the isolated state, in a form identical to its natural form, or modified compared with its natural form, but remaining cytocompatible with the skin irrespective of the mode by which it is obtained or produced.

Thus, and in accordance with a first aspect, the invention concerns a composition comprising,
- at least one basic amino acid, advantageously selected from the group constituted by arginine, lysine, histidine, ornithine and hydroxyproline; and
- at least one glycosylceramide.

In accordance with a particular embodiment, the composition in accordance with the invention is a cosmetic or dermo-pharmaceutical composition, advantageously cosmetic.

The amino acids are completely biomimetic active principles because they are found in all living organisms, either as protein constituents or in the free form following a process of degradation of a living organism.

In the context of the invention, the term "basic amino acid" designates any form of the amino acid, including any salt.

Glycosylceramides are glycolipids constituted by a ceramide bonded via a beta-oside (β-oside) bond to a single neutral ose (monoglycosylceramide) or to several neutral oses (polyglycosylceramide), a ceramide being the amide of a sphingosine and a fatty acid. Advantageously, the neutral ose is a hexose or a deoxyhexose selected from the group constituted by allose, altrose, glucose, mannose, gulose, idose, galactose, fucose and fructose. The fatty acid advantageously has a long chain and in general contains 16 to 18 carbon atoms, the chain optionally being hydroxylated. Preferably, the ceramides are selected from the group comprising ceramide-1, ceramide-2, ceramide-3, ceramide-4, ceramide-5, ceramide-6, ceramide-7.

Glycosylceramides are found in all organisms, in particular human beings, where they are particularly abundant in the nerve and brain tissues in the capacity of constituents of the myelin sheath. For this reason, glycosylceramides are considered to be biomimetic compounds.

In accordance with a particular embodiment, the basic amino acid comprised in the composition in accordance with the invention is arginine or one of its salts.

In general, the various forms of arginine are D-arginine, D,L-arginine and L-arginine. Examples of organic or mineral salts of arginine which may be cited are hydrochlorides, glutamates, butyrates and glycolates.

Advantageously, the composition in accordance with the invention contains L-arginine.

In accordance with a particular embodiment, the arginine used in the composition in accordance with the invention is in the purified form, preferably with a purity equal to at least 60%, preferably equal to at least 70%, advantageously equal to at least 80%, even more advantageously equal to at least 90%, or even equal to at least 95% or even 98%. The arginine contained in the composition in accordance with the invention may be of plant or chemical origin, or in fact obtained by biotechnology. Thus, the cosmetic starting material L-Arginine marketed by Kyowa Hakko Kogyo Co., Ltd and having the INCI name arginine may be used in the composition in accordance with the invention.

In accordance with a particular embodiment, the composition in accordance with the invention comprises at least one glycosylceramide in the form of a monoglycosylceramide and/or a polyglycosylceramide, advantageously a monoglycosylceramide and/or tetraglycosylceramide.

In accordance with a preferred embodiment, the composition in accordance with the invention comprises glycosylceramides in the monoglycosylceramide and tetraglycosylceramide form.

In accordance with a particular embodiment, the composition comprises a monoglycosylceramide corresponding to a glucuronic acid (or gluconic acid) covalently bonded to a ceramide via a β-oside bond.

In accordance with a particular embodiment, the polyglycosylceramide in accordance with the invention corresponds to an oligosaccharide covalently bonded to a ceramide via a β-oside bond.

Advantageously, the polyglycosylceramide in accordance with the invention is a tetraglycosylceramide the oligosaccharide of which corresponds to the following concatenation of oses: glucuronic acid-glucosamine-galactose-mannose (or GlcA-GlcN-Gal-Man).

In accordance with a particular embodiment, the glycosylceramide or glycosylceramides in accordance with the invention are in the purified form, with a purity equal to at least 60%, preferably equal to at least 70%, advantageously equal to at least 80%, even more advantageously equal to at least 90%, or even equal to at least 95%.

The glycosylceramide or glycosylceramides comprised in the composition in accordance with the invention may be of plant or vegetable origin, or in fact obtained by biotechnology.

Advantageously, the composition in accordance with the invention comprises at least one glycosylceramide of biotechnological origin.

Advantageously, all of the glycosylceramides comprised in the composition in accordance with the invention are of biotechnological origin.

In accordance with a particular embodiment, the glycosylceramides of the invention are of biotechnological origin, in particular obtained by extraction from membranes of bacterial species that synthesize them, such as *Pseudomonas* spp, for example. Advantageously, the glucosylceramides are obtained from the bacterial species *Pseudomonas paucimobilis*. Thus, the cosmetic starting materials Glycosphingolipid and Biosphingo, respectively marketed by THREE B CO., INC AND KIKKOMAN BIOCHEMIFA COMPANY, and having the INCI name glycosphingolipids, may be used in the composition in accordance with the invention.

In accordance with a particular embodiment, the at least one basic amino acid, advantageously arginine or one of its salts, represents between 0.001% and 2% of the total weight of the composition, advantageously between 0.01% and 0.5%.

In accordance with another particular embodiment, at least one glycosylceramide, advantageously glycosylceramides in the monoglycosylceramide and tetraglycosylceramide form, represents between 0.0001% and 1% of the total weight of the composition, advantageously between 0.001% and 0.1%.

In a particular embodiment, the composition in accordance with the invention further comprises at least one triterpene saponoside or one of its derivatives selected from the group constituted by glycyrrhetinic acid, glycyrrhizin, stearyl glycyrrhetinate and dipotassium diglycyrrizinate.

These compounds, which are obtained from licorice, have anti-inflammatory properties and are routinely used in the topical treatment of atopic dermatitis in order to combat the itching associated with this skin condition. By way of example, the cosmetic starting materials 18β-glycyrrhetic acid, dipotassium glycyrrhizinate and glycyrrhizic acid and respectively corresponding to the INCI names glycyrrhetinic acid, dipotassium glycyrrhizate and glycyrrhizic acid and stearyl glycyrrhetinate (all designated by their INCI name and commercially available from the producers listed, for example, in the International Buyer's Guide from the INCI), may be used in the compositions in accordance with the invention.

Advantageously, in addition to the basic amino acid and the at least one glycosylceramide, the composition in accordance with the invention comprises a combination of glycyrrhetinic acid and dipotassium diglycyrrizinate in the capacity of anti-inflammatory agents.

In accordance with a particular embodiment, at least one triterpene saponoside or one of its derivatives represents between 0.0001% and 10% of the total weight of the composition, advantageously between 0.01% and 5%, preferably between 0.05% and 1%.

In accordance with one embodiment, the composition in accordance with the invention comprises, in addition, at least one non-ionic surfactant selected from saccharose esters and/or sorbitan esters.

In accordance with a particular embodiment, the at least one non-ionic surfactant in accordance with the invention represents between 0.1% and 5% of the total weight of the composition, advantageously between 1% and 3%.

Suitable saccharose esters and/or sorbitan esters for use in accordance with the invention are described in detail in the document WO 2014/023895 which is incorporated in its entirety by reference. These agents, used alone or in combination, can be used to reduce adhesion and/or proliferation of *Staphylococcus aureus* on the skin and/or on the nasal mucosae, subsequently improving the general clinical context of atopic dermatitis.

In accordance with a preferred embodiment, the non-ionic surfactant of the invention corresponding to a sorbitan ester is polysorbate 20 (INCI) or polysorbate 80 (INCI), advantageously polysorbate 20.

In accordance with another preferred embodiment, the non-ionic surfactant of the invention corresponding to a saccharose ester is a sucrostearate with a Hydrophilic Lipophilic Balance (HLB) of at least 16, which corresponds to a relative proportion of sucrose monoesters to stearic acid comprised between 75% and 80% by weight of sucrose stearate (INCI).

In accordance with a particular embodiment, the non-ionic surfactant of the invention represents between 0.1% and 5% by weight of the composition, advantageously between 1% and 3%.

In accordance with a particular embodiment, the composition in accordance with the invention comprises, in addition, at least one lipid which is capable of restoring the skin barrier, advantageously selected from the group constituted by:
- at least one lipid which is exogenous to the skin, advantageously a vegetable oil;
- a mixture of constituents which are naturally present in the skin, comprising ceramide-1, ceramide-3, ceramide-6; cholesterol; free fatty acids and phytosphingosine; and
- squalane.

In a particular embodiment, the lipids which are exogenous to the skin correspond to sunflower seed oil (INCI: *Helianthus annuus* seed oil), oilseed rape oil (INCI: canola oil) and/or jojoba oil (INCI: *Simmondsia chinensis* (jojoba) seed oil). These three vegetable oils have known emollient and anti-inflammatory properties.

In a particular embodiment, the mixture of constituents which are naturally present in the skin is in the form of a composition containing lipids with the following INCI names: Sodium Lauroyl Lactylate, Ceramide NP, Ceramide AP, Phytosphingosine, Cholesterol, Ceramide EOP.

In a particular embodiment, the lipid which is capable of restoring the skin barrier is squalane, a lipid which is also found in the composition of the skin. The squalane in the context of the invention is advantageously of vegetable origin.

Preferably, the lipids which are capable of restoring the skin barrier represent between 0.01% and 25% by weight of the composition, advantageously between 1% and 15%.

In accordance with a particular embodiment, the composition of the invention comprises, in addition, at least one additional polyhydroxylated selected from the group comprising rhamnose, xylitol and mannitol. These polyhydroxylated compounds contribute to reducing the adhesion of pathogenic bacteria such as *S. aureus*, to the skin and mucosae in human beings, including the nasal mucosae. Mannitol has a radical scavenging activity.

In a particular embodiment of the invention, the composition comprises a mixture of the three additional polyhydroxylated compounds cited above. Advantageously, the rhamnose represents between 0.01% and 1% of the total weight of the composition, the xylitol represents between 0.05% and 2% of the total weight of the composition and the mannitol represents between 0.005% and 1% of the total weight of the composition.

Advantageously, the composition of the invention additionally comprises vitamin PP, also known as vitamin B3, nicotinamide or niacinamide, or one of its derivatives; these compounds are known to stimulate the synthesis of the lipids of the stratum corneum such as ceramides, free fatty acids and cholesterol. Vitamin PP acts by stimulating the activity of serine palmitoyl transferase, a key enzyme in the synthesis of sphingosine, a precursor molecule of ceramides.

In accordance with a particular embodiment, the niacinamide and/or one of its derivatives represents between 0.001% and 10% of the total weight of the composition, advantageously between 0.01% and 5%, preferably between 0.1% and 2%.

In accordance with a particular embodiment, the composition of the invention comprises prebiotic substances, in particular oligosaccharides such as fructooligosaccharides or FOS (INCI), short chain dextrins (INCI), arabinogalactans (INCI), inulin (INCI) or lactulose (INCI). In a preferred embodiment, the composition in accordance with the invention contains FOS, i.e. oligomers of fructose and saccharose with a degree of polymerisation comprised between 2 and 10. FOSs contribute to the induction of β-defensins and are also metabolised by saprophytic flora. FOSs have antimicrobial properties and can be used to reduce the use of artificial preservatives, as described in the document FR 2 831 059.

Advantageously, FOSs represent between 0.001% and 20% of the total weight of the composition, advantageously between 0.01% and 10%, preferably between 0.1% and 5%.

In accordance with a particular embodiment, the composition in accordance with the invention additionally comprises at least one antimicrobial peptide inducer, i.e. an active ingredient which is capable of inducing the synthesis and/or secretion of antimicrobial peptides in human beings (in particular, β-defensins) or by the microbiota. These properties have been demonstrated in particular in plant extracts such as the extract from *Peumus boldus* (boldo) or the extract from *Filipendula ulmaria* (meadowsweet).

Advantageously, the antimicrobial peptide inducer is boldo extract, meadowsweet extract or a mixture thereof.

In accordance with a particular embodiment, the antimicrobial peptide inducer represents between 0.001% and 5% of the total weight of the composition, preferably between 0.01% and 1%.

In accordance with a particular embodiment, the composition in accordance with the invention is in a form which is adapted to be cosmetically and/or dermatologically acceptable, i.e. compatible with the skin, the mucosae, the hair, the naps and/or the scalp.

In accordance with a preferred embodiment, the composition in accordance with the invention is in a form which is suitable for topical administration.

In another embodiment, the advantageously cosmetic composition in accordance with the invention additionally comprises a bioactive system combining, on the one hand, a stable form, in aqueous solution, of a nucleotide selected from ATP (adenosine triphosphate), Gp4G (diguanosine tetraphosphate) and Ap4A (diadenosine tetraphosphate); and on the other hand, at least one biomimetic peptide comprising at most six amino acids, advantageously different from those of the invention, imitating a skin polypeptide or a skin protein, or an agonistic or antagonistic biomolecule of said peptide or said protein. In practice, the combination of these active principles means that the metabolic activity of the cells of the skin can be catalysed while obtaining a dermo-cosmetic or therapeutic effect because of the use of the biomimetic peptides. These latter may be selected in order to obtain the desired effect, for example an inhibitory effect on irritations of neurogenic origin, a depigmentation activity, an effect inhibiting any intolerance or sensitisation, etc.

In practice, in the bioactive system in accordance with the invention, the nucleotide represents at most 10% of the total weight of the composition, preferably between 0.001% and 5%; and the biomimetic peptide represents between 0.001% and 1% of the total weight of the composition.

In accordance with another embodiment, the composition in accordance with the invention may, in addition, comprise an extract from the bacterium *Arthrobacter agilis*, in particular an extract which is rich in carotenoids (INCI: Micrococcus lysate). Advantageously, the composition in accordance with the invention comprises a dry extract of this type which represents between 0.00001% and 0.1% of the total weight of the composition, preferably between 0.0001% and 0.001%.

In accordance with another embodiment, the composition in accordance with the invention additionally comprises other components which can contribute to internal protection by an action which may consist of protection of the DNA, a reduction in immunosuppression induced by UV radiation, a radical scavenging action or a combined effect of these actions.

The protective action of a preparation in accordance with the invention against oxidative stress or to counter the effect of free radicals may be further improved if it furthermore comprises one or more antioxidants, which will readily be selected by the person skilled in the art from the starting materials used in the cosmetics field.

In a particular embodiment of the invention, the composition in accordance with the invention also contains active principles which are capable of stimulating the proliferation of skin cells, advantageously fibroblasts and/or keratinocytes, preferably human or animal fibroblasts. In particular and in accordance with this embodiment, the composition in accordance with the invention comprises, in addition:
α-lipoic or one of its salts;
a derivative of vitamin C selected from ethyl ascorbic acid and sodium ascorbate, or a mixture thereof; and
hyaluronic acid, the molecular weight (Mw) of which is advantageously comprised between 0.5 and 15 kDa, preferably between 0.5 and 10 kDa.

Advantageously, the α-lipoic acid or one of its salts represents less than 0.1% of the total weight of the composition, advantageously less than 0.01%, preferably between 0.001% and 0.0005%.

Advantageously, the vitamin C derivative selected from ethyl ascorbic acid and sodium ascorbate or a mixture thereof, advantageously ethyl ascorbic acid, preferably 3-O ethyl ascorbyl ether, represents between 0.001% and 10% of the total weight of the composition, advantageously between 0.01% and 5%, preferably between 0.1% and 1%.

Advantageously, the hyaluronic acid, the molecular weight (Mw) of which is advantageously comprised between 0.5 and 15 kDa, preferably between 0.5 and 10 kDa, represents between 0.001% and 10% of the total weight of the composition, advantageously between 0.01% and 5%, preferably between 0.1% and 1%.

In accordance with another embodiment of the invention, the composition additionally comprises at least one, or even all of the following constituents exerting an in vivo biological effect on the cells of the skin, the lips, the haft and/or the mucosae subjected to UV-A and/or UV-B radiation, respectively:
a radical scavenger preserving the cell structures such as, for example, vitamin E and/or its liposoluble or hydrosoluble derivatives, in particular tocotrienol and/or tocopherol, advantageously representing between 0.001% and 10% of the total weight of the composition, even more advantageously between 0.02% and 2%, preferably 0.04%;
an agent which limits immunosuppression, such as vitamin PP, for example, advantageously representing between 0.001% and 1% of the total weight of the composition, preferably between 0.01% and 0.3%;
a protective agent for the p53 protein such as, for example, epigallocatechin gallate (EGCG), advantageously representing between 0.001% and 0.1% of the total weight of the composition, preferably between 0.005% and 0.05%.

The composition in accordance with the invention may also additionally comprise peptide extracts of soya and/or wheat.

In practice, the peptide extracts deriving from soya or wheat grains are obtained by an enzymatic hydrolysis of said grains via peptidases, which can be used to recover peptides with a mean size of 700 Da. Preferably, the soya peptide extract is the extract identified by the CAS number 68607-88-5 and/or the wheat peptide extract is the extract identified by the CAS number 70084-87-6. The wheat and soya extracts may correspond to the INCI names Hydrolyzed wheat protein and Hydrolyzed soy protein, respectively.

In a particular embodiment, the soya and wheat peptide extracts are used together, for example in a ratio by weight respectively comprised between 80/20 and 20/80, advantageously comprised between 70/30 and 30/70, preferably equal to 60/40.

In one advantageous embodiment, the soya and/or wheat peptide extracts are free from synthetic GHK tripeptides (glycyl-histidyl-lysine; INCI: Tripeptide-1). In practice, the peptide extracts of soya and/or wheat represent between 0.01% and 20% of the total weight of the composition, advantageously between 0.1% and 10%, preferably between 0.2% and 0.7%.

In accordance with an alternative embodiment and advantageously, the composition in accordance with the invention additionally comprises at least one UV filter. Filtering UV light is known to improve the general condition of the skin in individuals with atopic dermatitis.

In the context of the invention, the term "UV filter" encompasses organic or inorganic compounds which are capable of filtering UV-A, UV-B and/or UV-C.

In accordance with the invention, these may also be inorganic filters instead of chemical or organic filters.

The compositions in accordance with the invention may contain one or more broad spectrum UV filters, i.e. compounds or mixtures which absorb UV-A, UV-B, UV-C and possibly visible light.

Examples of broad spectrum organic filters which may be used in the context of the invention are filters corresponding to the following INCI names: tris biphenyl triazine, bis ethylhexyloxyphenol methoxyphenyl triazine, methylene bis-benzotriazolyl tetramethylbutylphenol. Another example of a broad spectrum filter which is suitable for the composition in accordance with the invention has the INCI name diethylhexyl butamido triazone.

Thus, and in a particular embodiment, the composition in accordance with the invention comprises at least one filter selected from the following group of compounds identified by their INCI name: tris biphenyl triazine, bis ethylhexyloxyphenol methoxyphenyl triazine, and methylene bis-benzotriazolyl tetramethylbutylphenol, diethylhexyl butamido triazone, or mixtures thereof.

Advantageously, the composition comprises the filter bis-ethylhexyloxyphenol methoxyphenyl triazine.

In accordance with another embodiment, in place of or in addition to broad spectrum filters, the composition contains at least one UV-A and/or UV-B filter, organic and/or inorganic, which may be in the aqueous phase (lipophilic) and/or oily phase (liposoluble).

Thus, and by way of example, the composition in accordance with the invention may contain liposoluble UV-B filters which are capable of contributing to the stabilisation or solubilisation of broad spectrum filters, or in fact to be reciprocally stabilised and for this reason, to increase the sun protection factor (SPF).

Advantageously, filters of this type correspond to the following INCI names: homosalate, octocrylene, ethylhexyl salicylate, ethylhexyl triazone.

In a preferred embodiment, the composition in accordance with the invention comprises ethylhexyl triazone.

In another embodiment, the liposoluble UV-B filter is α-(trimethylsilyl)-ω-(trimethylsilyloxy)poly[oxy(dimethyl)silylene]-co-[oxy(methyl)(2-{4-[2,2-bis(ethoxycarbonyl)vinyl]phenoxy}-1-methylene ethyl)silylene]-co-[oxy(methyl)(2-(4-[2,2-bis(ethoxycarbonyl)vinyl]phenoxy)prop-1-enyl)silylene], a silicone polymer which is capable of filtering in the UV-B (INCI: polysilicone-15).

In a preferred embodiment, the composition in accordance with the invention comprises at least one UV-B filter selected from the following group of compounds identified by their INCI name: homosalate, ethylhexyl salicylate, ethylhexyl triazone, polysilicone-15, or mixtures thereof.

In a particular embodiment, the composition is free from the following filters: 4-methylbenzylidene camphor, benzophenone-2, benzophenone-3, ethylhexyl methoxycinnamate, octocrylene.

In an advantageous embodiment, the composition in accordance with the invention comprises at least one UV-A filter, in order to ensure complete filtering of the harmful portion of the solar spectrum.

Advantageous UV-A filters in the context of the present invention are butyl methoxydibenzoylmethane (INCI) and diethylamino hydroxybenzoyl hexyl benzoate (INCI).

In a particular embodiment, the UV-A filter is bis-(diethylaminohydroxybenzoyl benzoyl) piperazine (INCI) (CAS number 919803-06-8).

Thus, and in a preferred embodiment, the composition in accordance with the invention comprises at least one filter selected from the following group of compounds identified by their INCI names: butyl methoxydibenzoylmethane, diethylamino hydroxybenzoyl hexyl benzoate, bis-(diethylaminohydroxybenzoyl benzoyl) piperazine, or mixtures thereof.

Other UV filters which are advantageous in the context of the present invention are hydrosoluble filters such as, for example:
  the filter corresponding to the INCI name disodium phenyl dibenzimidazole tetrasulfonate.
  the filter corresponding to the INCI name phenylbenzimidazole sulfonic acid, In a preferred embodiment, the composition in accordance with the invention comprises at least one hydrosoluble filter selected from the following group of compounds identified by their INCI names: disodium phenyl dibenzimidazole tetrasulfonate, phenylbenzimidazole sulfonic acid, or mixtures thereof.

Advantageously, the inorganic mineral filters, or mineral screens, are metallic oxides and/or other compounds which are difficult to dissolve or are insoluble in water, in particular oxides of titanium ($TiO_2$), zinc (ZnO), iron ($Fe_2O_3$), zirconium ($ZrO_2$), silicon ($SiO_2$), manganese (for example MnO), aluminium ($Al_2O_3$), or cerium ($Ce_2O_3$).

In accordance with a particular embodiment, the inorganic mineral screens may be used in the form of an oily or aqueous pre-dispersion which is commercially available. These pre-dispersions may advantageously be supplemented with dispersion aids and/or solubilisation mediators.

The inorganic mineral filters may also be surface treated or encapsulated, in order to provide them with a hydrophilic, amphiphilic or hydrophobic nature. This surface treatment may consist of providing the mineral screens with a thin inorganic and/or organic, hydrophilic and/or hydrophobic film.

In a preferred embodiment, the composition in accordance with the invention comprises at least one mineral screen selected from the following group of compounds identified by their INCI names: zinc oxide, titanium dioxide, or mixtures thereof.

The list of UV filters which has been cited which may be used in the context of the present invention are clearly given by way of non-limiting indication.

Advantageously, the UV filters as described above which are present in the composition in accordance with the invention represent between 0.1% and 30% of the total weight of the composition, advantageously between 0.5% and 20%, even more advantageously between 1% and 15%.

In accordance with a particular embodiment, the composition in accordance with the invention has a sun protection factor (SPF) which is greater than or equal to 10, preferably greater than or equal to 20, advantageously greater than or equal to 30, even more advantageously greater than or equal to 50.

In accordance with a preferred embodiment, the composition in accordance with the invention has a ratio of UV-A/UV-B protection which is greater than or equal to ⅓.

The sunscreen composition in accordance with the invention comprises at least one sunscreen solubiliser.

The composition in accordance with the invention may additionally comprise a SPF "booster", i.e. an agent which amplifies the sun protection factor, and/or a photostabiliser, i.e. an ingredient which can be used to increase the SPF or photostabilise the filters, an ingredient of this type not itself being considered to be a sun screen. Examples which may be cited are:

butyloctyl salicylate (INCI), the photostabiliser advantageously representing between 0.01% and 10% of the total weight of the composition, even more advantageously between 0.1% and 2%;

benzotriazolyl dodecyl p-cresol (INCI), the photostabiliser advantageously representing between 0.01% and 10% of the total weight of the composition, even more advantageously between 0.1% and 2%;

pongamol (INCI), a plant molecule absorbing in the UV-A, advantageously representing between 0.5 and 2% of the total weight of the composition, even more advantageously of the order of 1%;

ethylhexyl methoxycrylene (INCI), photostabiliser, solubiliser and SPF "booster" advantageously representing between 1% and 5% of the total weight of the composition;

a styrene acrylate copolymer (INCI: styrene/acrylate copolymer), preferably representing between 1% and 10% of the total weight of the composition in accordance with the invention;

diethylhexyl syringylidene malonate (INCI), advantageously representing between 1% and 10% of the total weight of the composition;

a hydrodispersible polyester, corresponding to the INCI names polyester-5 (and) Sodium silicoaluminate, advantageously representing between 1% and 10% of the total weight of the composition);

an acrylate copolymer with a glass transition temperature of −5° C. à −15° C. as measured by differential scanning calorimetry, said copolymer advantageously representing between 1% and 10% of the total weight of the composition.

In accordance with a particular embodiment, the composition of the invention additionally comprises an advantageously coloured particle with a blurring effect or a mixture of several particles with a blurring effect. These particles with a blurring effect are also termed "soft focus effect particles or indeed "haze effect particles".

In the context of the invention, the term "particle with a blurring effect" designates a particle, advantageously coloured, which is intended to provide the complexion with more transparency and a blurring effect. In particular, the particle with a blurring effect enables the composition containing it to attenuate the micro-relief of the skin by means of an optical effect, and in particular skin blemishes such as spots, wrinkles and fine lines.

A number of particles with a soft focus or blurring effect are commercially available. Examples which may be cited are starting materials from the Ronasphere range based on a silica substrate, marketed by MERCK, as well as a number of starting materials marketed by JGC-C&C (the Coverleaf range, based on sericite or sericite/talc), NIHON KOKEN (Relief Color Silséem range based on a mica/silica substrate), or MIYOSHI KASEI (PC-Bail range based on a silica substrate).

In accordance with yet another embodiment, the starting material KSP-100 marketed by SHINETSU having the INCI name Vinyl dimethicone/methicone silsesquioxane crosspolymer may be used in the capacity of a blurring effect particle.

Preferably, the blurring effect particles comprised in the composition of the invention represent between 0.5% and 20% of the total weight of the composition, advantageously between 1% and 10%, even more advantageously between 1% and 5%

In accordance with a particular embodiment, the composition in accordance with the invention may additionally comprise any fatty substance which is in routine use in the cosmetics field. Silicone fats such as oils, silicone gums and waxes may in particular be cited; as well as non-silicone fats such as oils and waxes of vegetable, mineral, animal and/or synthetic origin. The oils may be volatile or non-volatile. Hydrocarbons, esters and synthesized esters, fatty alcohols and fatty acids may also be cited.

In accordance with a particular embodiment, the composition may additionally comprise an aqueous medium, a hydroalcoholic medium containing an alcohol such as ethanol, or an organic medium comprising the usual organic solvents such as C1-6 alcohols, in particular ethanol and isopropanol, glycols such as propylene glycol, or ketones.

In accordance with a particular embodiment, the composition in accordance with the invention additionally comprises at least one conventional emulsifier selected from amphoteric, anionic, cationic or non-ionic emulsifier, used alone or as a mixture.

In accordance with a particular embodiment, the composition in accordance with the invention additionally comprises the usual adjuvants in the field under consideration, such as hydrophilic or lipophilic thickening agents or gelling agents, hydrophilic or lipophilic additives, active ingredients, in particular cosmetics, preservatives, antioxidants, fragrances, fillers, pigments, odour absorbers, colorants, moisturizing agents (glycerin), vitamins, essential fatty acids, liposoluble polymers, in particular hydrocarbons, opacifiers, stabilisers, sequestrating agents, conditioners and propellants.

Clearly, the person skilled in the art will be careful to select these possible adjuvants or excipients with a view to their being complementary in nature and/or with a view to their quantity in a manner such that the advantageous properties of the composition of the invention are not, or are not substantially altered by the envisaged additive.

The composition in accordance with the invention is advantageously formulated so as to be cosmetically acceptable, i.e. compatible with the skin, the mucosae, the hair and the scalp. Preferably, the composition of the invention is a composition for application to the skin or for topical use.

The term "composition for application to the skin" or "for topical use" designates a composition which is compatible with application to the skin, the mucosae, the hair and/or the scalp, preferably human skin.

The composition of the invention may be in any of the galenical forms which are appropriate for a topical application, in particular in the form of an aqueous, hydroalcoholic, organic or oily solution; a suspension or dispersion in solvents or fats, of the lotion or serum type; in the form of a vesicular dispersion; in the form of a water in oil (W/O) emulsion, an oil in water (O/W) or a multiple emulsion such as a water in oil in water (W/O/W) emulsion. The thickness of the emulsion may be variable and be in the form of a cream or milk; the composition of the invention may also be in the form of an ointment, a gel or a solid stick, pasty or solid anhydrous products, a foam, in particular an aerosol, in a two-phase composition or in fact in a sprayable composition.

The galenical form of the composition and its mode of preparation, and as a consequence the excipients which are appropriate for the composition of the invention, may be selected by the person skilled in the art on the basis of their general knowledge as regards the desired type of composition.

It may be particularly advantageous to formulate the composition of the invention in a manner such that it can be sprayed. This may, for example, be carried out by means of the formulation for specific emulsions comprising particular combinations of excipients.

In accordance with another aspect, the invention concerns a cosmetic treatment method consisting of applying a composition as defined above to the skin.

In accordance with another aspect, the invention concerns a composition, advantageously cosmetic, comprising at least one glycosylceramide, advantageously a monoglycosylceramide and/or a polyglycosylceramide, for the prevention and/or treatment of atopic dermatitis.

In accordance with a particular embodiment, the at least one glycosylceramide, advantageously a monoglycosylceramide and/or a polyglycosylceramide, is as described above.

The invention also concerns a method for the treatment of atopic dermatitis, consisting of applying the composition as defined above to the skin.

In accordance with another aspect, the invention concerns a composition, advantageously cosmetic, comprising:
  at least one basic amino acid selected from the group constituted by arginine, lysine, histidine, ornithine, hydroxyproline and one of their salts, and
  at least one glycosylceramide,
for use in the prevention and/or treatment of atopic dermatitis.

In accordance with another particular aspect, the invention concerns a composition comprising at least one glycosylceramide, advantageously a monoglycosylceramide and/or a polyglycosylceramide, preferably in combination with at least one basic amino acid selected from the group constituted by arginine, lysine, histidine, ornithine, hydroxyproline and one of its salts, for use in
  inducing the expression, or increasing the expression, of at least one gene coding for a constituent transmembrane protein of the tight junctions, advantageously claudin-1; and/or
  inducing an increase in the amount of at least one constituent transmembrane protein of the tight junctions, advantageously claudin-1; and/or
  improving the integrity of the tight junctions; and/or
  strengthening, improving the barrier function of the skin.

In accordance with a particular embodiment, the basic amino acid comprised in the composition for its use in accordance with the invention is arginine or one of its salts.

Advantageously, the composition for its use in accordance with the invention contains L-arginine.

In accordance with a particular embodiment, the composition for its use in accordance with the invention comprises at least one glycosylceramide corresponding to a monoglycosylceramide and/or polyglycosylceramide, advantageously a monoglycosylceramide and/or tetraglycosylceramide.

In accordance with a preferred embodiment, the composition for its use in accordance with the invention comprises glycosylceramides in the monoglycosylceramide and tetraglycosylceramide form.

In accordance with a particular embodiment, the composition for its use in accordance with the invention comprises a monoglycosylceramide corresponding to a glucuronic acid (or gluconic acid) covalently bonded to a ceramide via a β-oside bond.

In accordance with a particular embodiment, the polyglycosylceramide comprised in the composition for its use in accordance with the invention corresponds to an oligosaccharide covalently bonded to a ceramide via a β-oside bond.

Advantageously, the polyglycosylceramide comprised in the composition for its use in accordance with the invention is a tetraglycosylceramide the oligosaccharide of which corresponds to the following concatenation of oses: glucuronic acid-glucosamine-galactose-mannose (or GlcA-GlcN-Gal-Man).

The glycosylceramide or glycosylceramides comprised in the composition for its use in accordance with the invention may be of vegetable or chemical origin, or in fact obtained by biotechnology.

Advantageously, the composition for its use in accordance with the invention comprises at least one glycosylceramide of biotechnological origin.

Advantageously, all of the glycosylceramides comprised in the composition for its use in accordance with the invention are of biotechnological origin.

In accordance with a particular embodiment, the at least one basic amino acid, advantageously arginine or one of its salts, represents between 0.001% and 2% of the total weight of the composition, advantageously between 0.01% and 0.5%.

In accordance with another particular embodiment, the at least one glycosylceramide, advantageously glycosylceramides in the monoglycosylceramide and tetraglycosylceramide form, represents between 0.0001% and 1% of the total weight of the composition, advantageously between 0.001% and 0.1%.

In accordance with a particular embodiment, the composition for its use in accordance with the invention is as described above (see the first aspect of the invention).

Advantageously and in respect of these different therapeutic applications, the composition of the invention is in a galenical form adapted to topical administration.

One way of demonstrating the effect of the composition in accordance with the invention on the prevention and/or treatment of atopic dermatitis is, for example, an evaluation of the expression of at least one gene coding for a constituent transmembrane protein of the tight junctions such as claudin-1. Alternatively, it may concern a qualitative and/or quantitative analysis targeting at least one constituent transmembrane protein of the tight junctions such as claudin-1. An example which may be cited is an analysis by chromatography and/or mass spectrometry, by Western blot, or in fact by immunohistochemical labelling.

The manner of carrying out the invention and the advantages deriving from it will become apparent from the following exemplary embodiments, given by way of non-limiting indication with the aid of the accompanying figure.

EXAMPLES OF EMBODIMENTS

Example 1: Cosmetic Composition in the Context of the Invention—Spray

A composition in accordance with the invention is described in Table 1.

| Ingredient (INCI) | Weight (as a %) |
| --- | --- |
| Aqua/water/eau | qsp100 |
| Glycerin | 15.00 |
| Dipropylene glycol | 9.00 |
| Isostearyl isostearate | 2.00 |
| Propylheptyl caprylate | 1.999 |
| Squalane | 1.00 |
| Sodium cocoyl glutamate | 0.8825 |
| Glycyrrhetinic acid | 0.50 |
| Pentylene glycol | 0.50 |
| Ornithine | 0.30 |
| Disodium EDTA | 0.20 |
| Citric acid | 0.17 |
| Propanediol | 0.125 |
| Xanthan gum | 0.10 |
| Tocopherol | 0.036 |
| Lecithin | 0.0201 |
| *Helianthus annuus* (sunflower) seed oil | 0.015 |
| Glycosphingolipids | 0.007 |

Example 2: Composition Cosmetic in the Context of the Invention—Gel

A composition in accordance with the invention is described in Table 2.

| Ingredient (INCI) | Weight (as a %) |
| --- | --- |
| Aqua/Water/Eau | qsp 100 |
| Glycerin | 2.00 |
| Hydroxyethyl Acrylate/Sodium Acryloyldimethyl Taurate Copolymer | 1.125 |
| Isohexadecane | 0.765 |
| Titanium Dioxide [Nano] | 0.375 |
| Phenoxyethanol | 0.35 |
| 1,2-hexanediol | 0.26 |
| Lysine | 0.20 |
| Polysorbate 20 | 0.165 |
| Alumina | 0.045 |
| Glycosphingolipids | 0.005 |

Example 3: Cosmetic Composition in the Context of the Invention—O/W Emulsion A composition in accordance with the invention is described in Table 3.

| Ingredient (INCI) | Weight (as a %) |
| --- | --- |
| Aqua/water/eau | qsp 100 |
| Glycerin | 13.00 |
| *Brassica campestris* (rapeseed) seed oil | 11.00 |
| Paraffinum liquidum/mineral oil/huile minérale | 8.00 |
| Behenyl alcohol | 2.00 |
| Dipropylene glycol | 2.00 |
| Sucrose stearate | 2.00 |
| *Simmondsia chinensis* (jojoba) seed oil | 1.00 |
| Hydroxyethyl acrylate/sodium acryloyldimethyl taurate copolymer | 0.616 |
| Pentylene glycol | 0.50 |
| Acrylates/c10-30 alkyl acrylate crosspolymer | 0.30 |
| Caprylyl glycol | 0.2545 |
| 1,2-hexanediol | 0.25 |
| Arginine | 0.20 |
| Sodium citrate | 0.20 |
| Dipotassium glycyrrhizate | 0.10 |
| Glycyrrhetinic acid | 0.10 |
| Sodium lauroyl lactylate | 0.10 |
| Polysorbate 60 | 0.042 |
| Sorbitan isostearate | 0.042 |
| Citric acid | 0.040 |
| Tocopherol | 0.035 |
| Methylpropanediol | 0.0246 |
| Phytosphingosine | 0.02 |
| Triethyl citrate | 0.02 |
| *Helianthus annuus* (sunflower) seed oil | 0.015 |
| Ceramide NP | 0.01 |
| Ceramide AP | 0.006 |
| Cholesterol | 0.005 |
| Carbomer | 0.004 |
| Xanthan gum | 0.004 |
| Glycosphingolipids | 0.003 |
| Phenylpropanol | 0.0009 |
| Ceramide EOP | 0.00001 |

Example 4: Effect of the Composition in Accordance with the Invention on the Expression of the Protein Claudin-1 in an In Vitro Cell Model of Atopic Dermatitis

1. METHODS AND APPARATUS

1.1. Biological Model And Cell Lines

Cell Line:
  cell type: normal human epidermal keratinocytes (NHEK; reference: Bioalternatives K34 1), used at $3^{rd}$ passage—culture conditions: 37° C., 5% $CO_2$
  culture medium: Keratinocyte-SFM complemented with Epidermal Growth Factor (or EGF) at a concentration of 0.25 ng/mL, pituitary extract (PE) at a concentration of 25 μg/mL and gentamycin at a concentration of 25 μg/mL
  assay medium used for this example: Keratinocyte-SFM complemented with gentamycin at a concentration of 25 μg/mL.

A culture of normal human keratinocytes was produced in order to assay the substances; briefly, the protocol was as follows:
  induction of differentiation of the keratinocytes with 0.75 mM calcium for 24 h;
  treatment with the compounds, 1 hour before induction by the alarmins;
  treatment with the following alarmins: histamine, IL-33 and IL-1β, in the following respective concentrations: 50 μM, 100 ng/mL and 100 ng/mL, in order to induce the phenotype for atopic dermatitis, characterized by a drop in the expression of claudin-1.
  Immunolabelling of the claudin-1 was then carried out.

1.2. Active Compounds of the Composition in Accordance with the Invention

The compounds employed in this example, alone or in combination, are shown in Table 4 below.

| Active compounds in accordance with the invention | Stock solution | Assay concentrations |
| --- | --- | --- |
| Arginine | 10% in ultrapure water | 0.02%, 0.04%, 0.1% and 0.2% |
| Glycosylceramides | 5% in ultrapure water | 0.0003%, 0.0006%, 0.0015% and 0.003% |

1.3. Cytotoxicity Assay

Preliminary cytotoxicity assays were carded out on normal human keratinocytes in an assay medium which also comprised $CaCl_2$ at a concentration of 0.75 mM. These preliminary assays coupled MTT tetrazolium (3-(4,5-dimethylthiazol-2-yl)-2,5-diphenyl tetrazolium bromide) salt reduction method with morphological observations under a microscope.

At the end of treatment (72 h of incubation), the cells were incubated in the presence of MTT the transformation of which into blue crystals of formazan being proportional to the activity of the dehydrogenase succinate (mitochondrial enzyme). After dissociation of the cells and dissolving the formazan by adding DMSO, the optical density (OD), representative of the number of live cells and their metabolic activity, was measured with a spectrophotometer (VERSAmax, Molecular Devices) at 540 nm.

The results of the MTT viability assay and observations of cell layers resulted in selecting concentrations of active compounds in accordance with the composition of the invention to be assayed in the rest of the study for the compound of interest (see Table 2).

1.4. Culture and Treatment

The keratinocytes were then seeded into 96-well plates and cultured in a culture medium for 72 hours, then in the assay medium containing the $CaCl_2$ differentiation inducer (0.75 mM) for an additional 24 hours. The medium was then replaced with assay medium containing the $CaCl_2$ inducer (0.75 mM) and containing or not containing (control) the active compounds of the invention, alone or in combination, or the solvent control (DMSO assayed at 0.02%), then the cells were pre-incubated for 1 hour. The mixture of alarmins: histamine, IL-33 and IL-1β (in the following respective concentrations: 50 µM, 100 ng/mL and 100 ng/mL) was then added and the cells were incubated for 72 hours. At the same time, a non-stimulated/differentiated and non-inhibited control condition (assay medium without $CaCl_2$ and without alarmins) and a non-inhibited control condition (assay medium with $CaCl_2$ and without alarmins) were produced.

For each condition, the analysis was carried out from 30 image quantifications (n=30) except for the control conditions produced from 60 image quantifications (n=60). A first evaluation of the results was carried out by taking all of the quantifications into account, then a second solely with the results with replicated cultures, i.e. with 3 replications (n=3), except for the control conditions which were carried out with 6 replications (n=6).

1.5. In Situ Immunolabelling

After incubation, the medium was eliminated and the cells were rinsed, fixed and permeabilized. The cells were then labelled with primary antibody directed against claudin-1. This antibody was then revealed by a secondary antibody coupled to a fluorochrome (GAM-Alexa 488). At the same time, the nuclei of the cells were stained with Hoechst 33258 (bis-benzimide).

1.6. Microscope Observations and Image Analyses

Images were acquired with a high resolution imaging system, INCell Analyzer™2200 (GE Healthcare; 20× objective). For each well, 10 digital images were acquired.

Labelling was quantified by measuring the intensity of fluorescence of the proteins with respect to the total number of cells identified by staining with bis-benzimide (integration of digital data by the Developer Toolbox 1.5 software, GE Health Care).

1.7. Data Processing

The raw data were transferred and processed using Microsoft Excel® software.

The intergroup comparisons were carried out with the aid of the bilateral unpaired Student t-assay. The statistical analyses could be interpreted if n≥5. However, for n<5, the calculated data were provided by way of indication only.

Formulae used in this report:
The standard error of the mean (sem) represents the difference between the mean of the sample with respect to the mean of the true population. The sem is calculated by dividing the standard deviation (Sd) by the square root of the size of the sample in accordance with the following formula: sem=standard deviation (Sd)/√n;

The percentage viability was calculated using the following formula: viability (%)=(OD compound/OD control)×100;

The statistical significance threshold is as follows: ns: >0.0.5 (not significant); *=0.01 to 0.05 (significant); =0.001 to 0.01 (very significant); *=<0.001. (extremely significant). The significance was calculated by statistically comparing the difference between results for the active ingredients alone and the combination, for each dose.

Figure 1:
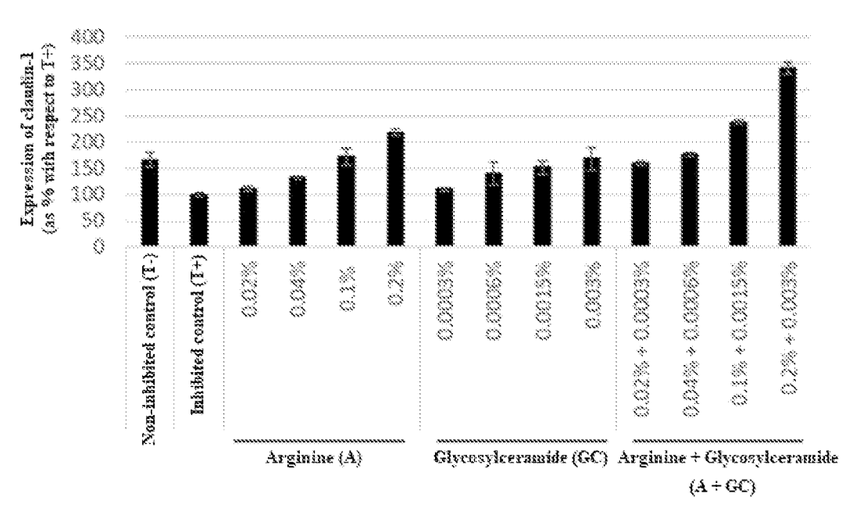
FIG. 1 shows the effect of arginine (A), glycosylceramides (GC), and their combinations (A+GC) on the expression of claudin-1 in a cellular model of atopic dermatitis. The "control" conditions correspond to the negative control (not inhibited or T$^-$) and to the positive control (inhibited or T$^+$). The percentage induction of the synthesis of claudin-1 is with respect to the positive inhibited control (100%).  indicates a statistical significance threshold p comprised between 0.001 and 0.01 (very significant) and * indicates a statistical significance threshold p<0.001 (extremely significant).

The results are shown in FIG. 1.

2. RESULTS

Under the control conditions, not stimulated/not differentiated by calcium ($CaCl_2$), the immunolabelling of the claudin-1 was present as spots in a few cells in the cytoplasm and occasionally in the membranes.

As expected, differentiation with $CaCl_2$ at a concentration of 0.75 mM induced an increase in the expression of the analysed tight junctions protein (claudin-1). This induction was strong and clearly significant and resulted in a large increase in the expression of claudin-1 at the membrane level, but also on the cytoplasmic level.

The treatment with the mixture of alarmins (histamine+ IL-1+IL-33 assayed at 50 µM+100 ng/mL+100 ng/mL) on the keratinocytes stimulated/differentiated by calcium ($CaCl_2$) at 0.75 mM induced a significant inhibiting effect as regards the expression of claudin-1 (mean about 61.5% for control).

The effect of the treatment with the active compounds of the invention, alone or in combination, on the expression of claudin-1 are shown in FIG. 1.

It can be seen from these results that the arginine (A) and the glycosylceramides (GC) assayed alone (% with respect to T+) significantly reversed the inhibiting effect of the mixture of alarmins on the expression of claudin-1.

The combination of arginine and glycosylceramides (A+GC) exerted an induction effect on the expression of claudin-1 which was greater than when these compounds were assayed alone. At all of the assayed concentration combinations, the increase was either very significant (*) or extremely significant () and, in each case more than simply complementary, indicating an unexpected potentializing synergy for the combination of arginine and glycosylceramides in the induction of the expression of claudin-1 and, as a consequence, on the strengthening of the barrier function of the skin and the prevention and/or treatment of atopic dermatitis.

BIBLIOGRAPHY

Batista, D. I. S., Perez, L., Orfali, R. L., Zaniboni, M. C., Samorano, L. P., Pereira, N. V., Sotto, M. N., Ishizaki, A. S., Oliveira, L. M. S., Sato, M. N., et al. (2015). Profile of skin barrier proteins (filaggrin, claudins 1 and 4) and Th1/Th2/Th17 cytokines in adults with atopic dermatitis. J. Eur. Acad. Dermatol. Venereol. 29: 1091-1095.

Brandner, J. M., Kief, S., Grund, C., Rendl, M., Houdek, P., Kuhn, C., Tschachler, E., Franke, W. W., and Moll, I. (2002). Organization and formation of the tight junction system in human epidermis and cultured keratinocytes. Eur. J. Cell Biol. 81: 253-263.

Cipriani, F., Dondi, A., and Ricci, G. (2014). Recent advances in epidemiology and prevention of atopic eczema. Off. Publ. Eur. Soc. Pediatr. Allergy Immunol. 25: 630-638.

Gruber, R., Börnchen, C., Rose, K., Daubmann, A., Volksdorf, T., Wladykowski, E., Vidal-Y-Sy, S., Peters, E. M., Danso, M., Bouwstra, J. A., et al. (2015). Diverse regulation of claudin-1 and claudin-4 in atopic dermatitis. Am. J. Pathol. 185: 2777-2789.

Halling-Overgaard, A.-S., Kezic, S., Jakasa, I., Engebretsen, K. A., Maibach, H., and Thyssen, J. P. (2017). Skin absorption through atopic dermatitis skin: a systematic review. Br. J. Dermatol. 177: 84-106.

Mack, M. R., and Kim, B. S. (2018). The Itch-Scratch Cycle: A Neuroimmune Perspective. Trends Immunol. 39: 980-991.

Mochizuki, H., Lavery, M. J., Nattkemper, L. A., Albornoz, C., Valdes Rodriguez, R., Stull, C., Weaver, L., Hamsher, J., Sanders, K. M., Chan, Y. H., et al. (2019). Impact of acute stress on itch sensation and scratching behaviour in patients with atopic dermatitis and healthy controls. Br. J. Dermatol. 180: 821-827.

Weidinger, S., Beck, L. A., Bieber, T., Kabashima, K., and Irvine, A. D. (2018). Atopic dermatitis. Nat. Rev. Dis. Primer 4: 1.

The invention claimed is:

1. A composition comprising:
   at least one basic amino acid selected from the group constituted by arginine, lysine, histidine, ornithine, hydroxyproline and one of their salts; and
   at least one glycosylceramide in the form of a monoglycosylceramide corresponding to a glucuronic acid covalently bonded to a ceramide, a polyglycosylceramide corresponding to an oligosaccharide covalently bonded to a ceramide, or a combination thereof.

2. The composition as claimed in claim 1, characterized in that the basic amino acid is arginine or one of its salts.

3. The composition as claimed in claim 1, characterized in that the polyglycosylceramide is in the form of a tetraglycosylceramide.

4. The composition as claimed in claim 1, characterized in that the glycosylceramide is in the form of a monoglycosylceramide and a tetraglycosylceramide.

5. The composition as claimed in claim 4, characterized in that:
   the oligosaccharide which is covalently bonded to the ceramide is glucuronic acid-glucosamine-galactose-mannose.

6. The composition as claimed in claim 1, characterized in that the at least one glycosylceramide is obtained by extraction from membranes of at least one bacterial species.

7. The composition as claimed in claim 1, characterized in that the at least one basic amino acid represents between 0.001% and 2% of the total weight of the composition.

8. The composition as claimed in claim 1, characterized in that the at least one glycosylceramide represents between 0.0001% and 1% of the total weight of the composition.

9. The composition as claimed in claim 1, further comprising:
   at least one triterpene saponoside or one of its derivatives selected from the group constituted by glycyrrhetinic acid, glycyrrhizin, stearyl glycyrrhetinate and dipotassium diglycyrrizinate;
   at least one non-ionic surfactant selected from sorbitan esters and/or saccharose esters, or
   a combination thereof.

10. The composition as claimed in claim 9, characterized in that:
    the at least one triterpene saponoside or one of its derivatives represents between 0.0001% and 10% of the total weight of the composition; and/or
    the at least one non-ionic surfactant represents between 0.1% and 5% of the total weight of the composition.

11. The composition as claimed in claim 9, characterized in that the non-ionic surfactant is polysorbate 20 or a sucrostearate with a Hydrophilic Lipophilic Balance (HLB) of at least 16.

12. The composition as claimed in claim 1, further comprising at least one lipid which is capable of restoring the skin barrier.

13. The composition as claimed in claim 1, characterized in that it is a cosmetic composition.

14. The composition as claimed in claim 1, characterized in that it is in a form which is suitable for topical administration.

15. A method for the prevention and/or treatment of atopic dermatitis in a subject in need thereof, comprising administering to the subject a composition comprising at least one monoglycosylceramide, a polyglycosylceramide, or a combination thereof.

16. The composition as claimed in claim 9, characterized in that the at least one glycosylceramide represents between 0.001% and 0.1% of the total weight of the composition.

17. The composition as claimed in claim 12, wherein the at least one lipid is selected from the group consisting of:
    a. a vegetable oil,
    b. a mixture comprising ceramide-1, ceramide-3, ceramide-6; cholesterol; free fatty acids, phytosphingosine, or a combination thereof;
    c. squalene, and
    d. combinations thereof.

18. The composition as claimed in claim 7, characterized in that the at least one basic amino acid represents between 0.01% and 0.5% of the total weight of the composition.

19. The composition according to claim 1, wherein the at least one basic amino acid is arginine.

20. The composition as claimed in claim 9, characterized in that:
   the at least one triterpene saponoside or one of its derivatives represents between 0.01% and 5% of the total weight of the composition; and/or
   the at least one non-ionic surfactant represents between 1% and 3% of the total weight of the composition.

* * * * *